United States Patent [19]

Johnston et al.

[11] Patent Number: 5,728,446
[45] Date of Patent: Mar. 17, 1998

[54] LIQUID MANAGEMENT FILM FOR ABSORBENT ARTICLES

[76] Inventors: Raymond P. Johnston; Robert T. Fehr; James A. Servatius, all of P.O. Box 33427, St. Paul, Minn. 55133-3427

[21] Appl. No.: 546,592

[22] Filed: Oct. 23, 1995

Related U.S. Application Data

[63] Continuation-in-part of Ser. No. 293,575, Aug. 22, 1993, Pat. No. 5,514,120.

[51] Int. Cl.⁶ .................. B32B 3/28; A61F 13/15
[52] U.S. Cl. .................. 428/167; 428/212; 428/213; 428/913; 604/378; 604/385.1
[58] Field of Search .................. 428/167, 172, 428/213, 156, 212, 332, 913; 604/378, 385.1, 380, 387

[56] References Cited

U.S. PATENT DOCUMENTS

| | | | |
|---|---|---|---|
| 2,915,554 | 12/1959 | Ahlbrecht et al. | 260/556 |
| 3,769,978 | 11/1973 | DeNight et al. | 128/287 |
| 3,881,490 | 5/1975 | Whitehead et al. | 128/287 |
| 4,323,069 | 4/1982 | Ahr et al. | 128/287 |
| 4,435,178 | 3/1984 | Fitzgerald | 604/365 |
| 4,643,727 | 2/1987 | Rosenbaum | 604/369 |
| 4,655,759 | 4/1987 | Romans-Hess et al. | 604/685 R |
| 4,676,786 | 6/1987 | Nishino | 604/378 |
| 4,678,464 | 7/1987 | Holtman | 604/385 R |
| 4,735,624 | 4/1988 | Mazars | 604/378 |
| 4,758,240 | 7/1988 | Glassman | 604/379 |
| 4,795,453 | 1/1989 | Wolfe | 604/385.1 |
| 4,798,604 | 1/1989 | Carter | 604/383 |
| 4,840,692 | 6/1989 | Kamstrup-Larsen | 156/252 |
| 4,908,026 | 3/1990 | Sukiennik et al. | 604/378 |
| 5,030,229 | 7/1991 | Yang | 604/385.1 |
| 5,037,409 | 8/1991 | Chen et al. | 604/358 |
| 5,383,314 | 1/1995 | Rothberg | 428/167 |
| 5,514,120 | 5/1996 | Johnston et al. | 604/378 |

FOREIGN PATENT DOCUMENTS

| | | | |
|---|---|---|---|
| 0 174 152 B1 | 7/1989 | European Pat. Off. | A61F 13/00 |
| 0 391 814 A2 | 10/1990 | European Pat. Off. | D01D 5/253 |
| 0 493 728 A1 | 7/1992 | European Pat. Off. | D04H 1/42 |
| 2082526 | 10/1971 | France | A41B 13/00 |
| 2603491 | 8/1977 | Germany. | |
| 2017505 | 10/1979 | United Kingdom | A61F 13/18 |
| WO 86/02543 | 5/1986 | WIPO | A61F 13/16 |
| WO 91/09580 | 7/1991 | WIPO | A61F 13/15 |
| WO 91/11161 | 8/1991 | WIPO | A61F 13/15 |
| WO 91/12949 | 9/1991 | WIPO | B29C 47/12 |
| WO 95/00093 | 1/1995 | WIPO | A61F 13/15 |

OTHER PUBLICATIONS

ASTM D 1505, Standard Test Method for Density of Plastics by the Density-Gradient Technique.
ASTM D 1238, Standard Test Method for Flow Rates of Thermo Plastics by Extrusion Plastometer.

*Primary Examiner*—Donald Loney
*Attorney, Agent, or Firm*—Gary L. Griswold; Walter N. Kirn; William J. Bond

[57] ABSTRACT

There is provided a liquid management film for use in rapid transport of liquid. The liquid management film is a thermoplastic film having at least one microstructured hydrophilic surface with a plurality of primary grooves. The primary grooves have at least two secondary grooves, each of said secondary grooves forming at least one notch which notches are substantially parallel and separated by a secondary peak. The notches or secondary grooves have an included angle of from about 10° to about 120°, the depth of one of said secondary grooves (the height of the secondary peak over the notch) being at least 5 microns and said depth being from about 0.5 to about 80 percent of the depth of the primary groove. The said notches have a radius of curvature of less than about 15 microns and the primary and/or secondary groove depth and width varies by less than 20 percent for each groove over a given length of the film.

28 Claims, 6 Drawing Sheets

LIQUID MANAGEMENT FILM FOR ABSORBENT ARTICLES

This is a continuation-in-part of application No. 08/293,575 filed Aug. 22, 1993, now U.S. Pat. No. 5,514,120.

BACKGROUND OF THE INVENTION

The present invention relates to liquid management films for liquid transport for use in articles such as absorbent articles such as meat tray liners, bed pads, baby diapers, sanitary napkins, and adult incontinent pads.

Disposable absorbent articles typically comprise three basic components: a liquid permeable topsheet that is located closest to the skin of the wearer when the article is in use, an absorbent core, and a liquid impermeable barrier sheet which is located on the opposite side of the absorbent core. Other components such as fastening tapes, leg and waist elastics, etc. are also commonly used.

The absorbent core receives and retains liquids that pass through the liquid permeable topsheet and typically comprises a batt of wood fluff fibers. Superabsorbent materials, typically in powder form, are often distributed within the absorbent core to enhance its liquid holding capacity and liquid retention properties.

One problem associated with absorbent articles is the inefficient utilization of the total absorptive capacity of the absorbent core material. This is due in part because absorbent articles normally have an elongated rectangular or hourglass shape and the liquid introduction or insult and spreading of liquid is often confined to the central area of the absorbent core.

Another problem associated with absorbent articles is the inability of the absorbent core to absorb liquids rapidly enough when large amounts of liquid are discharged into the absorbent core over short periods of time. This often results in undesirable side leakage.

To improve the liquid acquisition and lateral spreading properties of absorbent articles, many products have utilized a wicking layer of tissue or crepe or a nonwoven. This wicking layer can be located between the liquid permeable topsheet and the absorbent core, in the center of the absorbent core, or in the absorbent core in a location closer to the liquid impermeable barrier sheet. However, tissue, crepe or nonwovens tend to promote isotropic spreading of liquids. That is, liquid tends to spread at similar rates in both the lengthwise and width directions of the absorbent article. As a result, in many instances where the core is elongate, the liquid will leak beyond the side edges of the absorbent article before it has an opportunity to spread to the ends of the absorbent core. U.S. Pat. No. 4,643,727 proposes a wicking layer, such as paper toweling, wrapped around a plastic bubble layer. WO 86/02543 proposes a wicking layer of tissue covering a corrugated laminate coated with superabsorbent particles. In U.S. Pat. No. 5,037,409 (Chen) a flow modulating layer is proposed which is preferably formed of a hydrophilic melt-blown nonwoven microfiber web. Likewise, U.S. Pat. No. 4,908,026 proposes a "flow control layer" which is placed between the absorbent core and a perforated topsheet where the "flow control layer" is a melt-blown nonwoven, preferably treated to be hydrophilic.

Numerous other approaches have been suggested for improving the liquid distribution and absorption properties of absorbent articles. Many investigations have proposed the use of channels, reservoirs, apertures, etc., that have been introduced generally into the wood fluff absorbent core and occasionally into the tissue wicking layer by methods such as embossing, corrugation, cutting or folding. See, for example, U.S. Pat. Nos. 4,676,786 (Nishino), 4,678,464 (Holtman), 4,655,759 (Romans-Hess et al.), 5,030,229 (Yang), 3,769,978 (DeNight et al.), 4,758,240 (Glassman), 4,795,453 (Wolfe), U.K. Patent No. 2,017,505 (Fitzgerald) and WO 86/01378 (Kamstrup-Larson). In WO 91/11161 there is proposed corrugation of the nonwoven liquid permeable topsheet of an absorbent product.

U.S. Pat. No. 4,735,624 (Mazars) discloses a disposable diaper comprising an absorbent pad constituted by an absorbent material consisting essentially of hydrophilic fibers joined to one another to form a coherent mass. The pad is narrow in the crotch area and widens out in the front and rear areas of the diaper with branches.

The use of a plastic netting material to promote the unidirectional spreading of liquids in absorbent pads, is disclosed in European Patent No. 0 174 152 B1. The use of certain complex shaped fibers, in tow or staple form, that are capable of transporting liquid in absorbent articles are disclosed in European Patent Application (E.P.A.) No. 0 391 814 A2 (Phillips et al.) and WO 91/12949 (Thompson) (who discloses fibers or sheets with an extremely large ratio of surface area to mass), and E.P.A. No. 493 728 A1 which discloses a notched fiber with notch angles ($\alpha$) less than ($180°-2\theta$), where $\theta$ is the liquid fiber contact angle.

U.S. Pat. No. 4,798,604 (Carter) discloses a contoured polymeric film which is apertured and contains a pattern of raised areas that may be employed to form the body contacting surface, i.e., topsheet, in absorbent devices. Films have also been proposed as liquid distribution layers in absorbent articles in WO 95/00093 where a liquid distribution strip is used in association with an absorbent strip. The liquid distribution strip is shorter and wider than the absorbent strip. The two strips are located between the topsheet and the absorbent core of the absorbent article (e.g., a sanitary napkin). The liquid distribution strip can be a polyethylene film which can be apertured and in one alternative embodiment has troughs. In French Patent No. 2,082,526 a diaper or tampon is provided with a drain that is a pleated sheet of nonwoven placed in the absorbent pad.

Despite these previously known technologies, additional improvements to obtain more efficient and speedier absorption by absorbent cores without leaking are desired.

SUMMARY OF INVENTION

The present invention provides liquid management films that facilitate desired rapid and uniform anisotropic or directionally dependent distribution of liquids, and absorbent articles using these films that exhibit excellent liquid acquisition and distribution, resulting in greater effective absorption capacity and greater comfort for the wearer.

In brief summary, articles using the invention liquid management film typically comprise a liquid permeable topsheet, a backsheet, sometimes preferably liquid impermeable, and an absorbent core disposed between the topsheet and backsheet, wherein the article further comprises at least one liquid management film that promotes rapid directional spreading of liquids. The liquid management film is a sheet, typically flexible, having at least one microstructure-bearing hydrophilic surface with a plurality of primary grooves with nested secondary grooves therein. When an absorbent article is assembled, the hydrophilic surface is in contact with the absorbent core. In some embodiments, the liquid management film is preferably impermeable, i.e., although its surface is hydrophilic the film does not transmit liquid through its body from one surface to the other surface in undesirable fashion. In some embodiments, the liquid management film (which may be impermeable or not as desired) has one or more apertures therein to hermit controlled transmission of liquid therethrough in a desired manner.

The invention liquid management film has at least one microstructured hydrophilic surface with a plurality of primary grooves to promote the undirectional spreading of liquids, a plurality of said primary grooves, each primary groove having at least two secondary grooves. The secondary grooves each forming at least one notch which notches are substantially parallel and separated by a secondary peak which secondary grooves have an included angle of from about 10° to about 120°. The depth of one of the secondary grooves (the height of the secondary peak over the notch) is at least 5 μm and generally about 0.5 to about 80 percent of the depth of the primary grooves. The notches have a radius of curvature of less than about 15 microns. Generally the primary or secondary grooves can be V-shaped or rectangular. Generally only the secondary grooves include notches.

Articles of the invention may be made in the form of meat tray liners, bed pads, diapers, adult incontinent devices, and feminine hygiene products.

BRIEF DESCRIPTION OF DRAWINGS

The invention will be further explained with reference to the drawing, wherein.

These figures, which are idealized, are not to scale and are intended to be merely illustrative and non-limiting.

DETAILED DESCRIPTION OF ILLUSTRATIVE EMBODIMENTS

Liquid management films of the invention are in the form of sheets or films rather than a mass of fibers. The grooves of liquid management films of the invention provide more effective liquid flow than is achieved with webs or tows formed from fibers. The walls of channels or grooves formed in fibers will exhibit undulations and complex surfaces that interfere with flow of liquid through the channels or grooves. In contrast, the grooves in the invention sheets or films are uniform and regular along substantially each groove length and preferably from groove to groove.

Liquid management films of the present invention are capable of spontaneously and uniformly transporting liquids along the axis of the film grooves. Two general factors that influence the ability of liquid management films to spontaneously transport liquids (e.g., water, urine or vaginal secretions) are 1) the geometry of the surface (capillarity, shape of the grooves) and 2) the nature of the film surface (e.g., surface energy).

Figure 1:
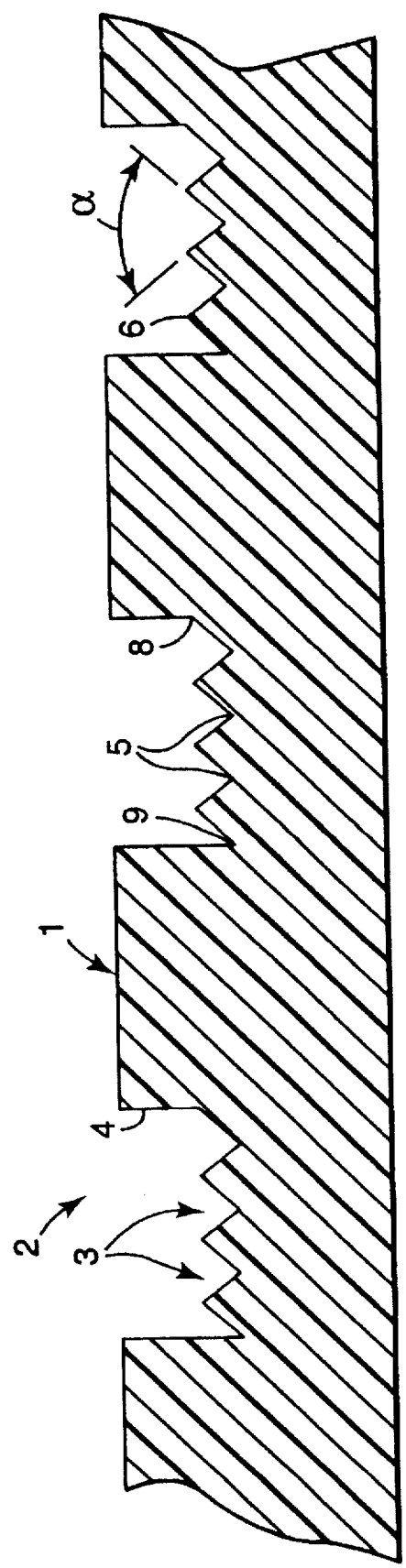
FIGS. 1, 2 and 3 are cross-sectional cutaway views of illustrative embodiments of liquid management films of the invention.

The grooves of liquid management films of the present invention can be of any geometry that provides desired liquid transport, and preferably one which is readily replicated. With reference to FIG. 1, one preferred geometry is a rectilinear primary groove or channel 2 in a flat film 1. The primary groove 2 has included secondary grooves 3 which forms a multitude of notches 5. The notches 5 (or secondary grooves 3, where the grooves are V-shaped and have substantially straight sidewalls) have an included angle of (i.e., angle Alpha) from about 10° to about 120°, preferably from about 10° to about 100°, and most preferably from about 20° to about 95°. The notch included angle is generally the secant angle taken from the notch to a point 2 to 1000 microns from the notch on the sidewalls forming the notch, preferably the included angle is the secant angle taken at a point halfway up the secondary groove sidewalls. It has been observed that notches with narrower included angular widths generally provide greater vertical wicking distance. However, if Alpha is too narrow, the wicking action will become significantly lower. If Alpha is too wide, the notch or secondary groove may fail to provide desired wicking action. As Alpha gets narrower, the contact angle of the liquid need not be as low, to get similar liquid transport, as the contact angle must be for notches or grooves with higher angular widths.

The primary groove included angle is not critical except in that it should not be so wide that the primary groove is ineffective in channeling liquid. Generally, the primary groove maximum width is less than 3000 microns and preferably less than 1500 microns. The included angle of a V-groove shaped primary groove will generally be from about 10 degrees to 120 degrees, preferably 30 to 90 degrees. If the included angle of the primary groove is too narrow, the primary groove may not have sufficient width at its base so that it is capable of accommodating an adequate number of secondary grooves. Generally, it is preferred that the included angle of the primary groove be greater than the included angle of the secondary grooves so as to accommodate the two or more secondary grooves at the base of the primary groove. Generally, the secondary grooves have an included angle at least 20 percent smaller than the included angle of the primary groove (for V-shaped primary grooves).

The depth of the primary grooves (2, 22) (the height of the peaks or tops above the lowermost groove notch), "d", is substantially uniform, and is typically from about 50 to about 3000 microns, preferably from about 75 to about 1500 microns, and most preferably is from about 100 to about 1000 microns. It will be understood that in some embodiments films with grooves (2, 22) having depths larger than the indicated ranges may be used. If the grooves are unduly deep, the overall thickness of the liquid management film will be unnecessarily high and the film may tend to be stiffer than is desired. The width of the primary groove at its base is sufficient to accommodate two or more secondary grooves.

When used in absorbent articles it is typically preferred that the liquid management films be thin and flexible to avoid imparting undesirable stiffness to the absorbent articles. For instance, in the case of liquid management films used in infant diapers or adult incontinent devices, the average film thickness from the front face to the back face of the film typically ranges from about 25 to about 1500 microns, preferably from about 125 to about 1000 microns. The liquid management film should be sufficiently thick to retain its structural integrity when subjected to stresses (e.g., stretching and flexing) expected to be encountered during use. A preferred liquid managebent film has a plurality of parallel thin film regions (e.g., which can be down to about 10 microns thick) with thicker film regions forming the primary and secondary peaks. These thin film regions are formed with rectangular shaped secondary grooves where the secondary groove bottoms (generally at least 3 microns wide, preferably at least 5 microns wide) define the parallel thin regions. This provides a film with improved flexibility even when the average film thickness is on the higher end of the above range. In the case of bed pads, the absorbent article need not be as highly flexible to provide comfort and the liquid management film may be up to 3000 microns or more thick.

The invention liquid management films can be formed from any thermoplastic materials suitable for casting, or embossing including, for example, polyolefins, polyesters, polyamides, poly(vinyl chloride), etc. Polyolefins are preferred, particularly polyethylene or polypropylene, blends and/or copolymers thereof, and copolymers of propylene and/or ethylene with minor proportions of other monomers, such as ethylene/vinyl acetate. Polyolefins are preferred because of their excellent physical properties, ease of processing, and typically lower cost than other thermoplastic materials having similar characteristics. Polyolefins readily replicate the surface of a casting or embossing roll. They are tough, durable and hold their shape well, thus making such films easy to handle after the casting or embossing process. Alternatively, liquid management films can be cast from curable resin materials such as acrylates or epoxies, and cured by exposure to heat or UV or E-beam radiation. Preferably, the liquid management film substantially retains its geometry and surface characteristics upon exposure to liquids.

Figure 8A:
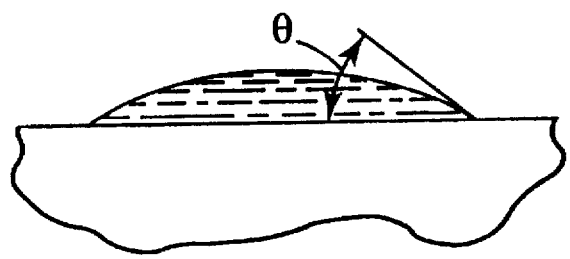
FIGS. 8a and 8b are schematic diagrams used to illustrate interaction of a liquid on a surface.
Figure 8B:
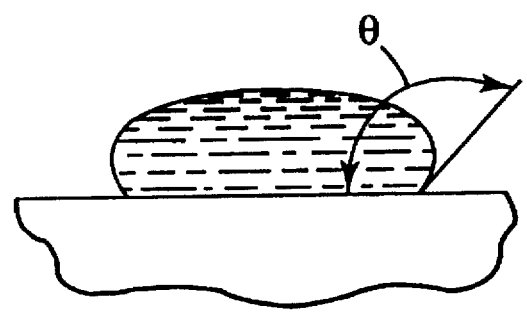

Generally, the susceptibility of a solid surface to be wet out by a liquid is characterized by the contact angle that the liquid makes with the solid surface after being deposited on the horizontally disposed surface and allowed to stabilize thereon. It is sometimes referred to as the "static equilibrium contact angle", sometimes referred to herein merely as "contact angle". As shown in FIGS. 8a and 8b, the contact angle Theta is the angle between a line tangent to the surface of a bead of liquid on a surface at its point of contact to the surface and the plane of the surface. A bead of liquid whose tangent was perpendicular to the plane of the surface would have a contact angle of 90°. Typically, if the contact angle is 90° or less, as shown in FIG. 8a, the solid surface is considered to be wet by the liquid. Surfaces on which drops of water or aqueous solutions exhibit a contact angle of less than 90° are commonly referred to as "hydrophilic". As used herein, "hydrophilic" is used only to refer to the surface characteristics of a material, i.e., that it is wet by aqueous solutions, and does not express whether or not the material absorbs aqueous solutions. Accordingly, a material may be referred to as hydrophilic whether or not a sheet of the material is impermeable or permeable to aqueous solutions. Thus, hydrophilic films used in liquid management films of the invention may be formed from films prepared from resin materials that are inherently hydrophilic, such as for example, poly(vinyl alcohol). Liquids which yield a contact angle of near zero on a surface are considered to completely wet out the surface. Polyolefins, however, are typically inherently hydrophobic, and the contact angle of a polyolefin film, such as polyethylene or polypropylene, with water is typically greater than 90°, such as shown in FIG. 8b. Body liquids that will come into contact with the liquid management films of the present invention are aqueous. Thus, if such films are used as liquid management films of the invention, they must be modified, e.g., by surface treatment, application of surface coatings, or incorporation of selected agents, such that the surface is rendered hydrophilic so as to exhibit a contact angle of 90° or less, thereby enhancing the wetting and liquid transport properties of the liquid management film.

In liquid management films of the invention, the desired surface energy of the microstructured surface of V-grooved liquid management films is such that:

Theta≦(90°—Alpha/2), wherein Theta is the contact angle of the liquid with the film and Alpha ($\alpha$) is the average included angle of the secondary V-groove notches.

Any suitable known method may be utilized to achieve a hydrophilic surface on liquid management films of the present invention. Surface treatments may be employed such as topical application of a surfactant, plasma treatment, grafting hydrophilic moieties onto the film surface, sol-gel coating, corona or flame treatment, etc. Alternatively, a surfactant or other suitable agent may be blended with the resin as an internal additive at the time of film extrusion. It is typically preferred to incorporate a surfactant in the polymeric composition from which the liquid management film is made rather than rely upon topical application of a surfactant coating. Topically applied coatings tend to fill in, i.e., blunt, the notches of the channels, thereby interfering with the desired liquid flow to which the invention is directed. An illustrative example of a surfactant that can be incorporated in polyethylene liquid management films is TRITON™ X-100, an octylphenoxypolyethoxyethanol nonionic surfactant, e.g., used at between about 0.1 and 0.5 weight percent. An illustrative method for surface modification of the films of the present invention is the topical application of a 1 percent aqueous solution of the reaction product comprising 90 weight percent or more of:

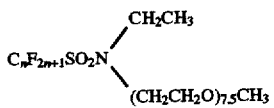

wherein n=8 (97 percent), n=7 (3 percent), and 10 weight percent or less of:

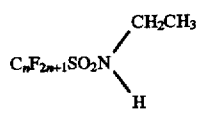

wherein n=8 (97 percent), n=7 (3 percent). Preparation of such agents is disclosed in U.S. Pat. No. 2,915,554 (Ahlbrecht et al.)

Figure 2:
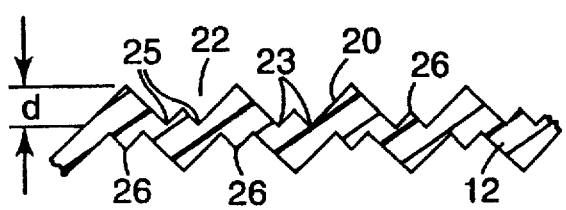
Figure 3:
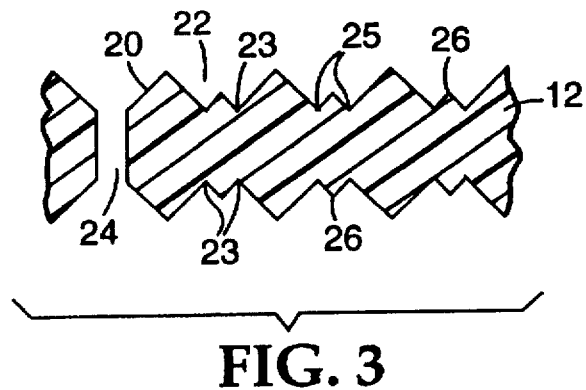

In some embodiments, the liquid management film 1 will have primary grooves or channels on only one major surface as shown in FIG. 1. In other embodiments, however, liquid management film (1, 12) will have primary grooves or channels on both major surfaces, as shown in FIGS. 2 and 3. Typically in the case of absorbent articles such as diapers, if the film has primary channels or grooves on both major surfaces, the primary channels or grooves on one surface are substantially parallel to those on the other surface. The primary channels or grooves 22 may be laterally offset from one surface to the other surface as shown in FIG. 2 or may be aligned directly opposite each other as shown in FIG. 3. A liquid management film with offset grooves or channels as shown in FIG. 2 provides a maximum amount of surface area for wicking while at the same time using a minimum amount of material. In addition, a liquid management film with offset channels or grooves can be made so as to feel softer, due to the reduced thickness and boardiness of the sheet, than a liquid management film with aligned channels as shown in FIG. 3. As shown in FIG. 3, liquid management films 12 of the invention may have one or more apertures 24 therein, which enable a portion of the liquid in contact with the front surface of the liquid management film to be transported to the back surface of the film, to improve liquid control. The apertures need not be aligned with the notch of a channel and do not need to be of about equal width as the channels. The surfaces of the liquid management film within the apertures is preferably hydrophilic.

In each primary groove 2 are at least two secondary grooves (3, 23) and at least two notches (5, 25), the notch (5, 25) or notches of each secondary groove (3, 23) is separated by a secondary peak (6, 26). Generally, each secondary groove will generally have only one notch, but a secondary groove will have two notches if the secondary groove is rectangular. The secondary peak (6, 26) for V-groove shaped secondary grooves is generally characterized by an included angle $\beta$ which is generally equal to $(\alpha^1+\alpha^2)/2$ where $\alpha^1$ and $\alpha^2$ are the included angles of the two adjacent V-groove shaped secondary grooves (3, 23), assuming that the two sidewalls forming each secondary groove are symmetrical and not curved. Generally, the angle $\beta$ would be from about 10° to about 120°, preferably from about 10° to about 90°, and most preferably from about 20° to about 60°. The secondary peak could also be flat (in which case the included angle would theoretically be 0°) or even curved, e.g., convex or concave, with no distinct top or included angle. Preferably, there are at least three secondary grooves (3, 23) and/or at least three notches for each primary groove (2, 22), included any notches (5, 25) associated with the end grooves (notches 8 or 9) as shown in FIG. 1.

The depth of one of the secondary grooves (3, 23) (the height of the top of the secondary peaks 6 over the notches 5) is uniform over the length of the liquid management films, and is typically at least 5 microns. The depth of the secondary grooves (3, 23) is generally 0.5 to 80 percent of the depth of the primary grooves, preferably 5 to 50 percent. The spacing of the notches (5, 25) on either side of a peak 6 is also preferably uniform over the length of the liquid management film. Preferably the primary and/or secondary groove depth and width varies by less than 20 percent, preferably less than 10 percent for each groove over a given length of the liquid management film. Variation in the secondary groove depth and shape above this range has a substantial adverse impact on the rate and uniformity of liquid transport along the liquid management film. Generally the primary and secondary grooves are continuous and undisturbed.

Figure 6:
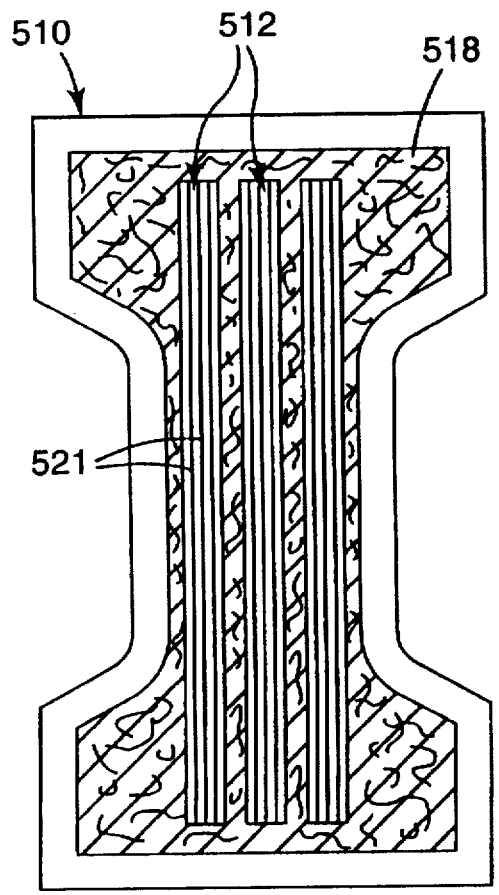
FIGS. 6 and 7 are elevational views of two other embodiments of diapers of the invention.
Figure 7:
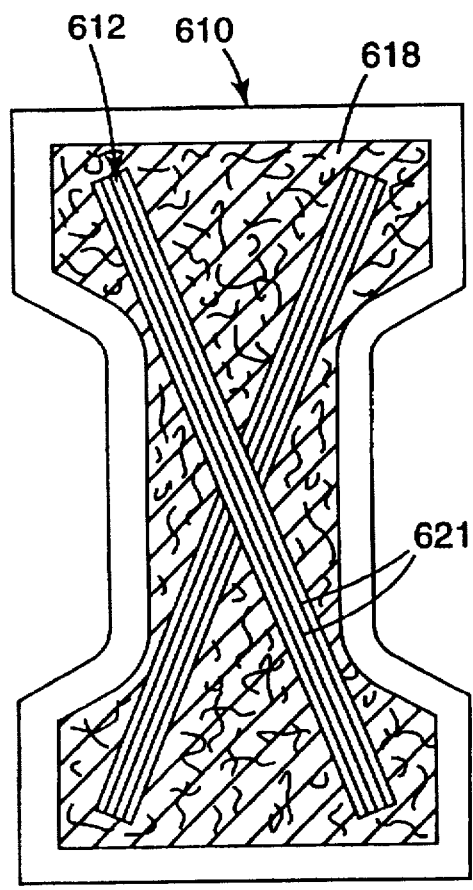
Figure 4:
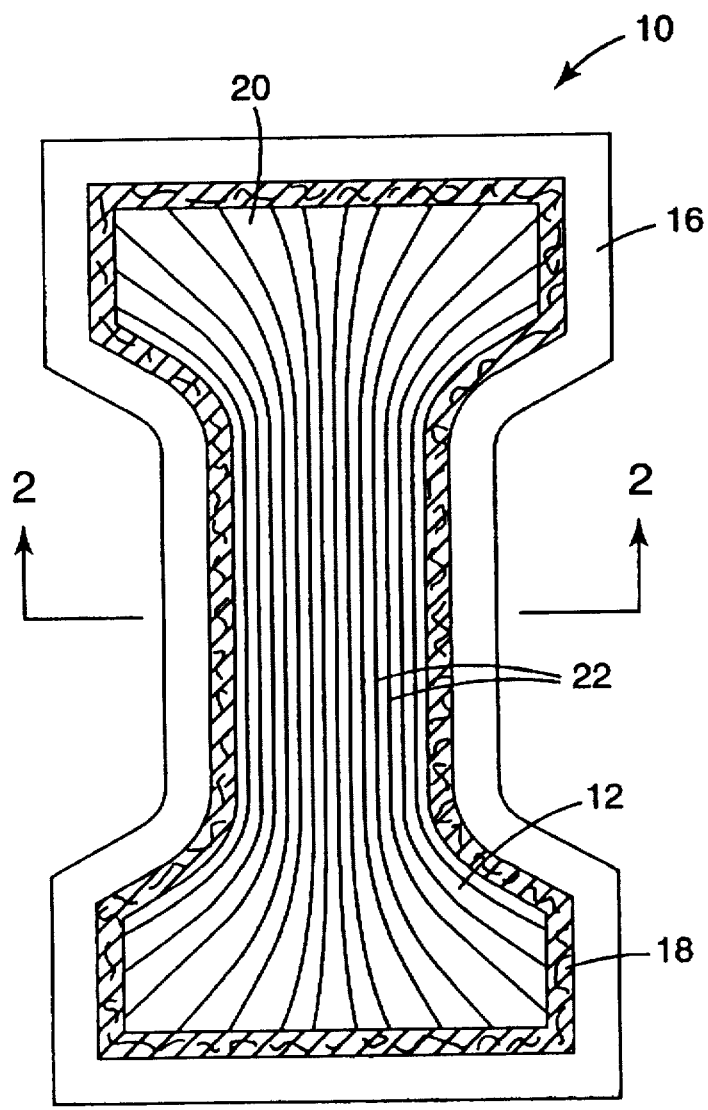
FIG. 4 is a elevational view of one embodiment of a diaper of the invention.
Figure 5:
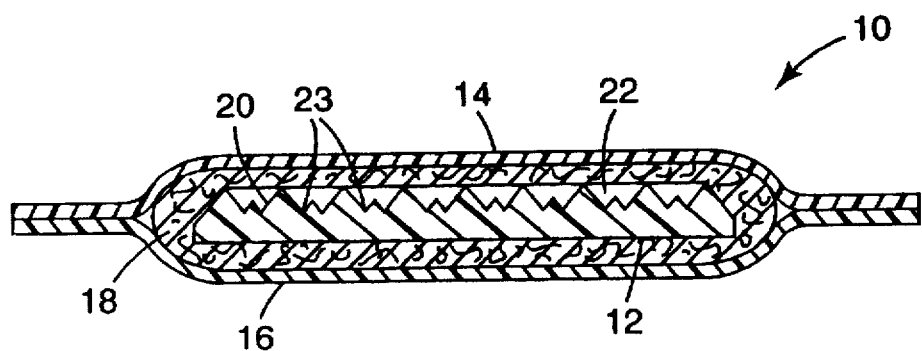
FIG. 5 is a cross-sectional illustration of the diaper of FIG. 4.

Liquid management film (1, 12) can be incorporated into a disposable absorbent article 10 in a number of ways. The film can be cut into one or more generally longitudinal strips that can be placed above, below, or within the absorbent core in a variety of configurations. Several illustrative embodiments are depicted in FIGS. 4, 6 and 7. FIGS. 4 and 5 show one embodiment of a diaper 10 comprising the invention liquid management film 12. Diaper 10 also comprises liquid permeable topsheet 14, liquid impermeable backsheet 16, and absorbent core 18. Diaper 510 in FIG. 6 has three liquid management films 512 with channels 521 arranged in parallel strips in absorbent core 518. Diaper 610 in FIG. 7 has two liquid management films 612 overlaid in an intersecting or "X" pattern in absorbent core 618. Typically, the intersection will be located where liquid introduction is expected.

Figure 12:
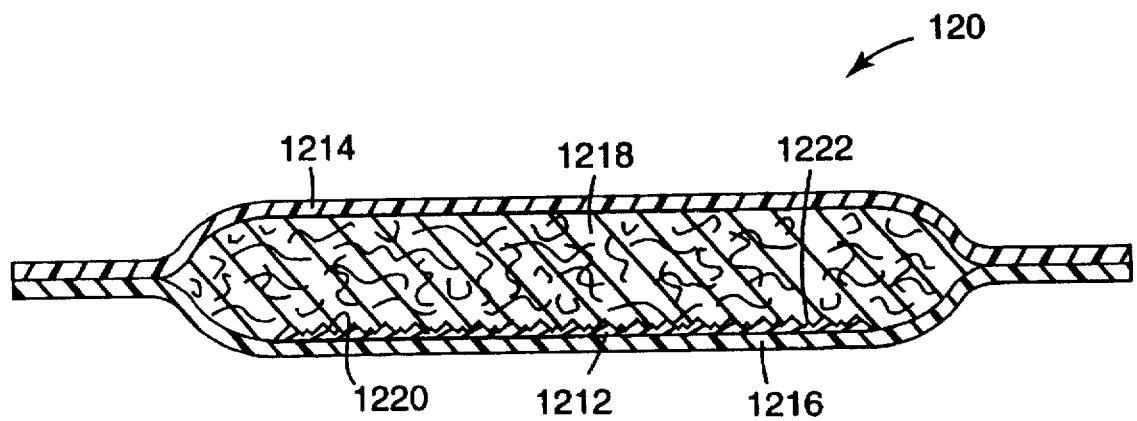
FIG. 12 is a cross-sectional illustration of another embodiment of a diaper of the invention.

If desired, the liquid management films may be disposed on the interior surface of the backsheet or even made integral therewith by forming the desired microstructured surface on the interior surface thereof. In this embodiment, the microstructured film serves two functions, as a liquid transport layer adjacent to the underside of the absorbent core and as a liquid barrier layer for the absorbent article. FIG. 12 illustrates diaper 120 comprising liquid permeable topsheet 1214, liquid impermeable backsheet 1216, and absorbent core 1218. Liquid management film 1212, with microstructured surface 1220 with primary grooves 1222, is disposed on the interior surface of backsheet 1216. If desired, grooves 1222 may be formed on the surface of backsheet 1216 such that the liquid management film and backsheet are of unitary construction.

A Preferred microstructure are ones in which the secondary grooves are V-shaped grooves or rectalinear shaped grooves, i.e., each groove is defined by at least a pair of planar walls which meet at at least one line of intersection which lines of intersection form a notch. Such channels are easily formed and provide rapid liquid transport. In other embodiments, the sides of the primary or secondary grooves need not be planar but each secondary groove preferably possesses at least one notch that extends parallel to the longitudinal axis of the groove. In other words, when viewed in cross-section, the line of intersection of a plane perpendicular to the axis of the groove and the walls of the groove preferably possesses an abrupt slope change, i.e., a geometric discontinuity or a point where the first order derivative of the surface of the groove has multiple values.

Although preferred, the notch need not be a perfect point; typically, useful liquid management is achieved if the notch has a radius of curvature of about 15 microns or less, preferably about 10 microns or less, and more preferably about 5 microns or less. It has been observed that coatings applied to microstructured surfaces to impart desired hydrophilicity thereto may tend to aggregate or pool in the base of the grooves, tending to increase the radius of curvature of the notch (3, 23).

Figure 9:
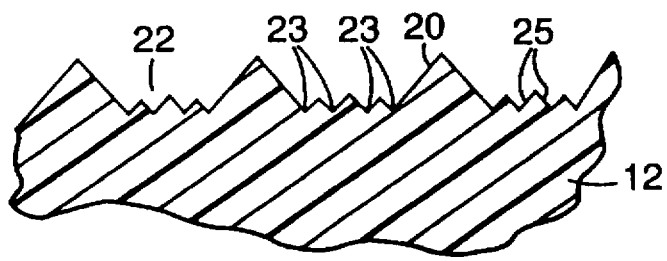
FIGS. 9 through 11 are cross-sectional illustrations of portions of films with channels having different cross-sectional profiles.
Figure 10:
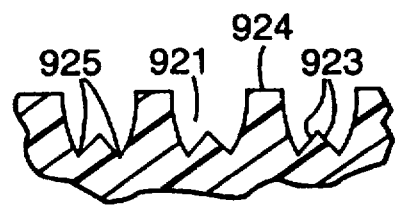

FIG. 9 shows a typical film with V-shaped primary and secondary grooves 22 and having a multitude of notches or abrupt slope changes 25. FIG. 10 shows a film with primary grooves 921 having non-planar, inwardly flaring walls and a base with abrupt slope change or notches 925 in secondary grooves 923. The liquid management film in FIG. 10 has large crests or tops 924 between adjacent primary grooves 921. It is typically preferred to have narrow crests or, as shown in FIG. 9, closely packed primary grooves such that the walls of adjacent channels are in contact in order to increase the number of grooves per unit surface width.

Figure 11:
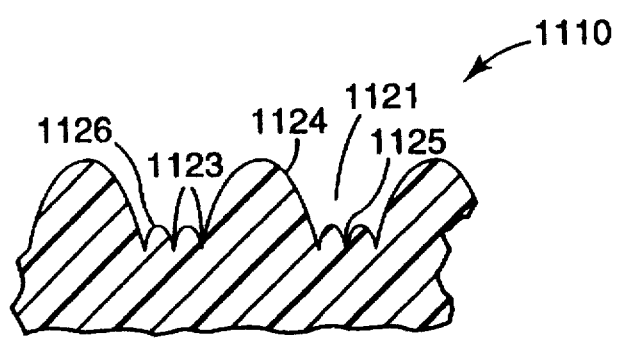

Preferably the primary and secondary groove walls are smooth because an excessive amount of surface roughness will tend to impede desired liquid flow. Liquid management films with groove walls that flare outwardly as shown in FIG. 11 are believed to provide an optimum combination of rapid anisotropic liquid flow and vertical wicking capability and accordingly are preferred for many applications. FIG. 11 shows a liquid management film 1110 with primary grooves 1121 with secondary grooves 1123 and notches 1125 and walls that flare outward rather than straight. For ease of manufacture the walls meet at secondary crests or peaks 1126 with a minimum of land area.

The primary and secondary grooves in the liquid management films of the invention are preferably oriented in the same direction, i.e., they are substantially parallel throughout their entire length. Grooves are considered to be substantially parallel as long as they extend in the same general direction without intersecting; their lateral spacing need not be equal over their entire length but the groove depth and shape is substantially uniform over the entire film length.

In a typical absorbent article of the invention as shown in FIG. 4, absorbent core 18 and liquid management film 12 are both elongate and oriented in the same general direction. It is typically preferred that the liquid management film be substantially coextensive with the absorbent core i.e., extend to within about 1 to 2 centimeters of the edge of the absorbent core in most cases. It is also typically preferred that it not extend beyond the absorbent core as this may result in leaking. In such instances, the grooves of the liquid management film will typically be oriented along the longitudinal axis of the film and of the absorbent core. Referring again to FIG. 4, it will typically be preferred in such instances for the lateral spacing of primary grooves 22 to vary along their longitudinal axis with the spacing being at a minimum in a longitudinally interior region of film 12 and being wider than the minimum at an exterior region of film 12. Such an article is typically constructed such that the region of minimum lateral spacing is located near expected liquid insult with the wider spacing being located at more distant locations. In such embodiments, liquid management film 12 provides both improved transport of the liquid away from the insult but also improved distribution of the liquid to more distant portions of absorbent core 18. If desired, additional primary grooves (not shown) may begin between the interior region and longitudinal edges of liquid management film 12.

Figure 13:
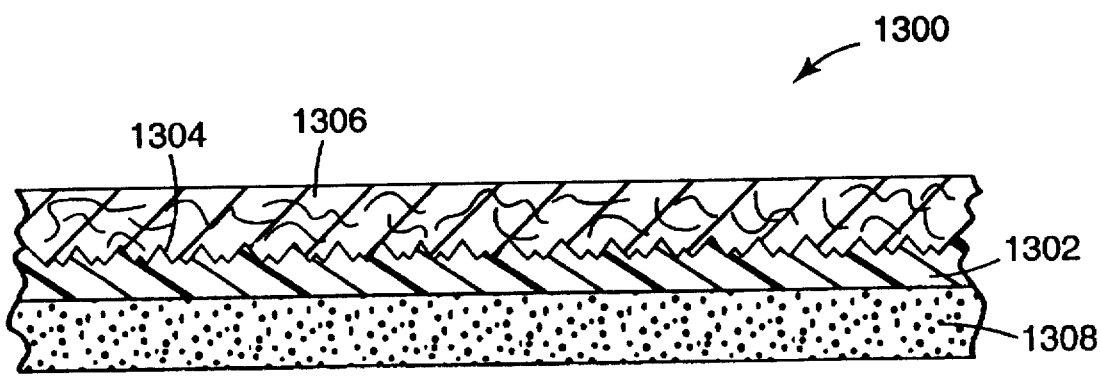
FIG. 13 is a cross-sectional illustration of another embodiment of an absorbent article of the invention.

FIG. 13 shows another embodiment of the invention with absorbent article 1300 comprising liquid management film 1302 with microstructure-bearing surface 1304, absorbent mass 1306, and attachment film 1308 on at least one side. Attachment film 1308 is selected in part based on the substrate to which the absorbent article is to be attached. Illustrative examples include suitable adhesives. Other illustrative examples include a component of a hook and loop fastening system, i.e., a strip of hook material with the strip of loop material being applied to a substrate.

Usually the microstructured surface is in contact with the absorbent core. However, in some embodiments, for instance where the absorbent material is subject to gel blocking, the liquid management film will be oriented such that a microstructure-bearing surface and the absorbent core are disposed on opposite sides of the liquid management film. In such embodiments, the liquid management film is preferably smaller than the absorbent core and/or has apertures therein. In some embodiments, the liquid management film may comprise another microstructure-bearing surface as described herein on the same side as the absorbent core.

In addition to absorbent articles with absorbent cores, the absorbent core could be an absorbent sheet or fabric such as might be found in a headband, wound dressing, wipe or towel. The invention liquid management film can be used for general purpose liquid removal, or drainage, or liquid delivery without a directly associated absorbent core. The liquid could be delivered to an absorbent body or a surface to which the liquid is delivered such as a substrate to be coated.

The invention liquid management film is formed by a replication process using a tool with a negative of the liquid management film microstructured grooves. The film is formed of a thermoplastic material by coating or thermal embossing using the reverse image tool.

In simple embodiments, absorbent articles may consist essentially of an absorbent core and liquid management film of the invention.

Various modifications and alterations of this invention will become apparent to those skilled in the art without departing from the scope and spirit of this invention.

TABLE I

|  | Pattern 1 | Pattern 2 | Pattern 5 | Pattern 6 |
| --- | --- | --- | --- | --- |
| Primary groove angular width (31) | 10° | 10° | 10° | 10° |
| Primary groove spacing (32) | 330 μm | 330 μm | 229 μm | 229 μm |
| Primary groove depth (33) | 635 μm | 635 μm | 203 μm | 203 μm |
| Notch included angle (34) | 95° | 95° | 95° | 95° |
| Secondary groove angular width (35) | 10° | NA | 95° | 112.5° |
| Secondary groove spacing (36) | 81 μm | NA | 50 μm | 50 μm |
| Secondary groove depth (37) | 127 μm | NA | 41 μm | 41 μm |
| Primary peak top width (38) | 29 μm | 29 μm | 29 μm | 29 μm |
| Secondary peak top width (39) | 29 μm | NA | 29 μm | NA |
| Primary groove base width (40) | 190 μm | 190 μm | 163 μm | 163 μm |
| Secondary groove base width (41) | 29 μm | NA | 13 μm | 16 μm |
| Primary groove wall angular width (42) | 10° | 10° | 10° | 10° |

EXAMPLES

Example 1 and Comparative Example 1

A liquid management film was prepared that had three small rectangular shaped grooves in the base of larger rectangular shaped main grooves. For comparison a liquid management film having rectangular shaped grooves was prepared that did not have secondary grooves in the base of the grooves.

Each liquid management film was prepared by pressing a 15 mil (0.38 mm) thick sheet of low density polyethylene (LDPE) film with a microstructured nickel tool having on its surface a pattern which was the negative impression of the desired pattern and groove geometry. The nickel tools were produced by shaping a smooth acrylic surface with diamond scoring tools to produce the desired microstructure pattern and then electroplating the structure to form a nickel tool suitable for microreplication. A cross-sectional view of Example 1 is illustrated generally in FIG. 14, except that there are three secondary grooves. The specifications of the tools used to form the Example 1 and comparative Example 1 liquid management films are given in Table I as Patterns 1 and 2, respectively, and are numerically indicated in FIG. 14. The LDPE used to press the samples was TENITE™ 1550P available from Eastman Chemical Co., which has a density of 0.918 gms/cm$^3$ (ASTM D1505) and a melt flow index of 3.5 gms/10 minutes (ASTM D1238, condition 190/2.16). 0.3 weight percent of TRITON™ X-100 surfactant (available from Union Carbide) had been blended with the polyethylene resin as an additive at the time that the film was extruded. The LDPE films were pressed with the microstructured nickel tool in a platen press for 30 seconds at 149° C. and 250 PSI, and then were immediately water cooled. Then resulting liquid management films were substantially exact replication of the microstructured tool such that the groove depth, width and overall shape did not significantly vary along the length of the film.

The liquid management films were tested for vertical wicking in accordance with DIN 53924 ("Deutsches Institut Fuer Normung"). The vertical height achieved in three minutes by a test fluid was measured. The test fluid used was deionized water containing 0.1 weight percent of a fluorescent dye, 2-(6-hydroxy-3-oxo-3H-xanthen-9-yl) benzoic acid disodium salt, a fluorescent disodium salt from Eastman Kodak Company. This liquid has been determined, using the Wilhelmy Balance Technique, to have a surface tension of about 74 to 75 dynes/centimeter.

The following vertical wicking results were obtained. The results are given in centimeters and represent an average of four tests carried out for each liquid management film type.

| Example | Pattern # | Vertical Wicking |
|---------|-----------|------------------|
| 1       | 1         | 12.4             |
| C1      | 2         | 4.3              |

The data shows that a liquid management film having small rectangular shaped secondary grooves in the base of larger rectangular shaped primary grooves had significantly improved vertical wicking performance compared to a liquid management film having rectangular shaped primary grooves that did not have secondary grooves.

Example 2 and Comparative Example 2

A liquid management film was prepared that had two small 40 degree V-groove shaped secondary grooves in the base of larger 60 degree V-groove shaped primary grooves. For comparison a liquid management film having 60 degree V-groove shaped primary grooves was prepared that did not have secondary grooves.

The liquid management films were prepared according to the method described above. The specifications of the tools used to form the V-groove shaped grooves are given in Table II (as Patterns 3 and 4). The liquid management film is substantially that depicted in FIG. 9 except that there are only two secondary grooves. As in Example 1 film, the groove depth, width and overall shape did not vary over the length of the film.

The liquid management films were tested for vertical wicking as described in Example 1. The following vertical wicking results were obtained. The results are given in centimeters and represent an average of four tests carried out for each liquid management film type.

| Example | Pattern # | Vertical Wicking |
|---------|-----------|------------------|
| 2       | 3         | 9.6              |
| C2      | 4         | 5.7              |

The data shows that a liquid management film having small V-groove shaped secondary grooves in the base of larger V-groove shaped primary grooves had improved vertical wicking performance compared to a liquid management film having V-groove shaped primary grooves that did not have secondary grooves.

TABLE II

|                                  | Pattern 3 | Pattern 4 |
|----------------------------------|-----------|-----------|
| Primary groove angular width     | 60°       | 60°       |
| Primary groove spacing           | 796 μm    | 796 μm    |
| Primary groove depth             | 635 μm    | 635 μm    |
| Notch included angle             | 40°       | 60°       |
| Secondary groove angular width   | 40°       | NA        |
| Secondary groove spacing         | 63 μm     | NA        |
| Secondary groove depth           | 178 μm    | NA        |
| Primary groove wall angular width| 60°       | 60°       |

Examples 3 and 4

Figures 14, 14A:
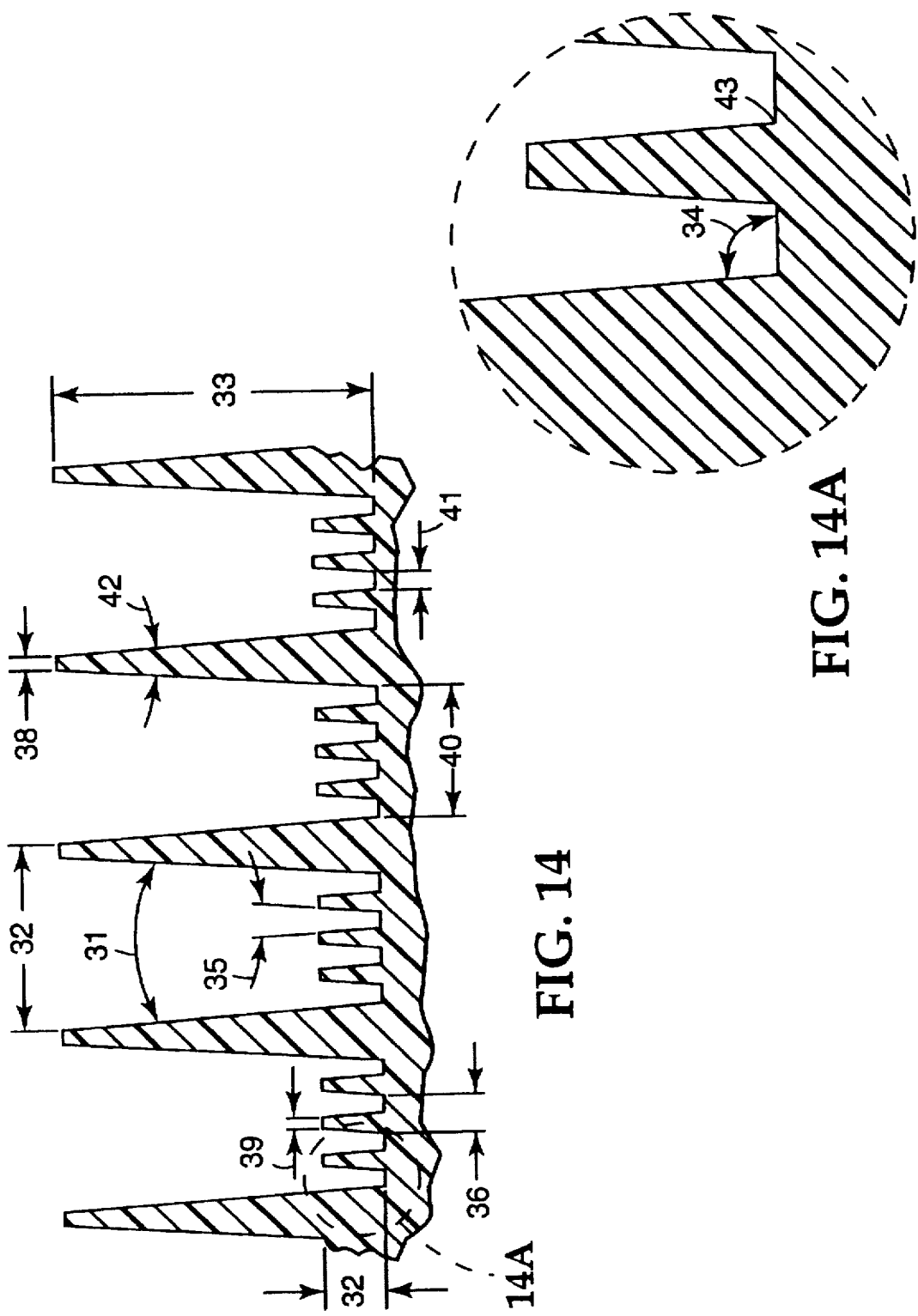
FIG. 14 is a cross-sectional view of another liquid management film of the invention.
FIG. 14A is a blow-up of a portion of the liquid management film of FIG. 14.

Tool Patterns 5 and 6 (see Table I) were used to prepare a liquid management film having four small rectangular shaped channels in the base of larger rectangular shaped main channels (Example 3) as shown in FIG. 14, except that with Example 4 the secondary peaks were sharp V shaped peaks rather the flat taped tapered secondary peaks shown in FIG. 14.

The film samples were prepared by cast extrusion of a LDPE resin onto a rotating forming roll using a standard single screw extruder, thus replicating the pattern on the surface of the roll which was the negative impression of the desired groove geometry and pattern. The temperature of the forming roll was maintained at 49° C. by standard means of internal cooling with circulating water. The LDPE resin used was TENITE™ 18BOA available from Eastman Chemical Co., having a density of 0.923 gms/cm³ (ASTM D1505) and a melt flow index of 20 gms/10 minutes (ASTM D1238, condition 190/2.16). Approximately 0.5 weight percent of TRITON™ X-100 surfactant was blended with the LDPE resin as an additive at the time of extrusion.

To assess the down web fidelity of the secondary groove structure for the liquid management films, notch radius of curvature measurements were obtained for each sample at locations along the length of three separate primary grooves of each liquid management film. The longitudinal spacing between the radius of curvature measurements for each groove was 20–25 cm.

The notch angle (34) used to measure the radius of curvature (43) is shown in FIG. 14, the notch adjacent the primary groove sidewall. The notch radius of curvature measurements of the liquid management films were obtained by taking a photomicrograph of the groove cross section with a scanning electron microscope. The liquid management films were potted in a dental impression resin which was allowed to cure. Then the sample was microtomed with a razor to leave an exposed cross section of the groove. A photomicrograph of this prepared sample was then taken. Tangent lines were drawn along several points of the tip of the groove. Normal lines to where the tangents contacted the groove were drawn and the location of their intersection identified as the center of curvature of the groove. An average arc radius was then fit to the tip curvature, with the center being the intersection of the normal lines. The arc radius length was then recorded as the radius of curvature.

The radius of curvature data (in microns) are summarized in Tables III and IV.

TABLE III

| Example 3 (Pattern 5) | Groove 1 | Groove 2 | Groove 3 |
| --- | --- | --- | --- |
| measurement 1 | 3.1 | 1.0 | 2.6 |
| measurement 2 | 1.0 | 1.2 | 2.2 |
| measurement 3 | 2.5 | 1.7 | 1.3 |

TABLE IV

| Example 4 (Pattern 6) | Groove 1 | Groove 2 | Groove 3 |
| --- | --- | --- | --- |
| measurement 1 | 2.6 | 3.2 | 2.4 |
| measurement 2 | 3.2 | 3.2 | 2.8 |
| measurement 3 | 3.2 | 2.2 | (not measured) |

Notch radius of curvature measurements and vertical wicking data were obtained for sheet samples of the Example 3 liquid management film before and after thermal treatment at several different temperatures. The sheet samples were heated in an oven for 50 minutes at temperatures of 90° C., 95° C., 100° C., 105° C., and 110° C. After air cooling, two or three notch radius of curvature measurements were obtained for each heat treated sample. Vertical wicking data was also obtained for each heat treated sample. Vertical wicking was measured as described in Example 1 except that the test fluid comprised 0.5 weight percent of sodium chloride and 0.1 weight percent of the fluorescent dye. The results reported are an average of three measurements. The radius of curvature data and vertical wicking data are summarized in Table V.

TABLE V

| Sample | Notch radius of curvature (microns) | Vertical wicking (cm) |
| --- | --- | --- |
| Example 3 (control) | 1.7, 1.2 (1.5 avg) | 8.2 |
| Example 3 after 90° C. | 4.2, 4.0 (4.1 avg) | 5.4 |
| Example 3 after 95° C. | 4.0, 4.1, 6.3 (4.8 avg) | 5.1 |
| Example 3 after 100° C. | 4.4, 6.9, 6.3 (5.9 avg) | 4.4 |
| Example 3 after 105° C. | 5.8, 6.7 (6.3 avg) | 4.5 |
| Example 3 after 110° C. | 13.0, 6.4 (9.7 avg) | 4.3 |

In a separate series of thermal treatments, sheet samples of the Example 3 fluid management film were subjected to temperatures >110° C. Samples were heated in an oven for 50 minutes at temperatures of 111° C., 112° C., 113° C., 114° C., and 115° C. After air cooling, notch radius of curvature measurements and vertical wicking data were obtained as described above. The data are summarized in Table VI.

TABLE VI

| Sample | Notch radius of curvature (microns) | Vertical wicking (cm) |
| --- | --- | --- |
| Example 3 after 111° C. | 10.9, 10.8, 12.2 (11.3 avg) | 6.9 |
| Example 3 after 112° C. | 13.1, 12.3, 13.1 (12.8 avg) | 6.8 |
| Example 3 after 113° C. | 12.0, 13.8, 13.2 (13.0 avg) | 6.6 |
| Example 3 after 114° C. | 12.0, 9.7, 9.2 (10.3 avg) | 3.7 |
| Example 3 after 115° C. | 78.4, 32.8, 78.9 (63.4 avg) | 2.2 |

Notch radius of curvature measurements and vertical wicking data were also obtained for samples of the Example 4 liquid management film before and after thermal treatment at several different temperatures. The samples were heated in an oven for 50 minutes at temperatures of 90° C., 95° C., 100° C., 105° C., and 110° C. After air cooling, two or three notch radius of curvature measurements were obtained for each heat treated sample. The average of these measurements is reported. Vertical wicking data was also obtained for each heat treated sample according to the method described for Example 3. The results reported are an average of three measurements. The radius of curvature data and vertical wicking data are summarized in Table VII.

TABLE VII

| Sample | Notch radius of curvature (microns) | Vertical wicking (cm) |
| --- | --- | --- |
| Example 4 (control) | 1.7 | 7.2 |
| Example 4 after 90° C. | 2.3 | 6.3 |
| Example 4 after 95° C. | 2.8 | 6.2 |
| Example 4 after 100° C. | 2.0 | 6.1 |
| Example 4 after 105° C. | 4.6 | 5.5 |
| Example 4 after 110° C. | 4.7 | 5.3 |

Thermal treatment of the liquid management films resulted in an increase in the radius of curvature values (decrease in notch sharpness) and a corresponding decrease in the vertical wicking capability of the channels. At 115° C. the Example 3 film became distorted resulting in significant loss in fidelity of the notch radius of curvature as well as the primary and secondary groove depth, width and overall shape.

Comparative Example 3

In an effort to prepare a liquid management film via a profile extrusion process, TENITE™ 1550P LDPE blended with 0.5% by weight TRITON™ X-100 was extruded through a die that had attached to the die lip the microstructured nickel tool that was used to prepare Example 2. A single screw extruder was used operating at a screw speed of 40 rpm to produce an output speed for the extruded strip of ~6.5 meters per minute. The extruded strip was immediately quenched in a cold (~10° C.) water bath.

Samples of the profile extruded strips were tested for vertical wicking as described in Examples 3 and 4. The samples did not vertically wick the fluid. It appeared that this process produced blunt notches which resulted in a dramatic reduction in vertical wicking capability compared to liquid management films that were prepared using a casting process.

What is claimed is:

1. A liquid management film for use in rapid transport of liquid comprising a thermoplastic film having at least one microstructured hydrophilic surface with a plurality of primary grooves to promote the undirectional spreading of liquids, a plurality of said primary grooves having at least two secondary grooves, each of said secondary grooves having at least two sidewalls the intersection of which forms at least one notch, which secondary groove notches are substantially parallel and separated by a secondary peak and which secondary groove notches or secondary grooves have an included angle of from about 10° to about 120°, the depth of one of said secondary grooves (the height of the secondary peak over the notch being at least 5 microns and said depth being from about 0.5 to about 80 percent of the depth of the primary groove, said notches having a radius of curvature of less than about 15 microns and the primary and/or secondary groove depth and width varies by less than 20 percent for each groove over a given length of the film.

2. The liquid management film of claim 1 wherein the primary grooves have a depth of from 50 to 3000 microns and the depth of the secondary grooves is from 5 to 50 percent of the depth of the primary grooves.

3. The liquid management film of claim 1 wherein the secondary grooves are V-shaped or rectangular.

4. The liquid management film of claim 2 wherein the primary grooves are V-shaped having an included angle of from about 10° to about 120°.

5. The liquid management film of claim 2 wherein the primary grooves are rectangular.

6. The liquid management film of claim 2 wherein the included angles of said secondary grooves or notches are between about 10° and 100°.

7. The liquid management film of claim 2 wherein where the included angles of said secondary grooves or notches are between about 20° and 95°.

8. The liquid management film of claim 2 wherein where the width and depth of each of said primary grooves varies by less than 10 percent over the length of said film.

9. The liquid management film of claim 2 wherein said primary grooves are between about 50 and about 3000 microns deep.

10. The liquid management film of claim 2 wherein said primary grooves are between about 75 and about 1500 microns deep.

11. The liquid management film of claim 2 wherein said primary grooves are between about 100 and about 1000 microns deep.

12. The liquid management film of claim 4 wherein the angular width of said primary grooves is between about 30° and about 90°.

13. The liquid management film of claim 2 wherein said secondary grooves notches included angle is a secant angle taken from the notch to points halfway up the secondary groove sidewalls.

14. The liquid management film of claim 2 where in said notches have a radius of curvature of about 10 microns or less.

15. The liquid management film of claim 2 wherein said notches have a radius of curvature of about 5 microns or less.

16. The liquid management film of claim 2 wherein said secondary grooves have a plurality of outwardly flaring walls.

17. The liquid management film of claim 2 wherein said film is impermeable to aqueous liquids.

18. The liquid management film of claim 2 wherein said liquid management film has an average thickness of between about 25 and 1500 microns.

19. The liquid management film of claim 18 wherein said liquid management film has an average thickness of between about 125 and 1000 microns.

20. The liquid management film of claim 2 wherein said liquid management film has one or more apertures therein.

21. The liquid management film of claim 2 wherein said liquid management film is made of one or more polyolefins.

22. The liquid management film of claim 2 wherein each of said primary grooves has three or more secondary grooves defining three or more notches.

23. The liquid management film of claim 2 wherein each of said primary grooves has three or more notches.

24. The liquid management film of claim 2 wherein said film is flexible.

25. The liquid management film of claim 2 wherein the depth of the secondary grooves is 5 to 50 percent of the depth of the primary grooves.

26. The liquid management film of claim 4 wherein the primary grooves have an angular width greater than the angular width of the secondary grooves.

27. The liquid management film of claim 1 wherein the secondary grooves are substantially rectangular and each has two notches.

28. The liquid management film of claim 24 wherein the secondary grooves are substantially rectangular and each has two notches where the bottoms of the rectangular grooves are at least 3 microns wide to form parallel thin film regions.

* * * * *